(12) United States Patent
Veenstra et al.

(10) Patent No.: US 11,412,971 B2
(45) Date of Patent: Aug. 16, 2022

(54) ECG CONNECTOR AND ECG CABLE

(71) Applicant: KONINKLIJKE PHILIPS N.V., Eindhoven (NL)

(72) Inventors: Hugo Veenstra, Kleine Brogel (BE); Frank Verbakel, Helmond (NL); Pierre Hermanus Woerlee, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 66 days.

(21) Appl. No.: 16/274,293

(22) Filed: Feb. 13, 2019

(65) Prior Publication Data

US 2019/0254549 A1  Aug. 22, 2019

(30) Foreign Application Priority Data

Feb. 20, 2018 (EP) .................................... 18157601

(51) Int. Cl.
*A61B 5/30* (2021.01)
*A61B 5/25* (2021.01)
*A61B 5/0535* (2021.01)
*A61B 5/08* (2006.01)
(Continued)

(52) U.S. Cl.
CPC .............. *A61B 5/25* (2021.01); *A61B 5/0535* (2013.01); *A61B 5/0809* (2013.01); *A61B 5/282* (2021.01); *A61B 5/303* (2021.01); *A61B 2562/225* (2013.01); *H01R 24/20* (2013.01); *H01R 2201/12* (2013.01)

(58) Field of Classification Search
CPC .............. A61B 5/0408; A61B 5/04085; A61B 5/04286; A61B 5/0535; A61B 5/0809; A61B 2562/225; A61B 5/25; A61B 5/303; A61B 5/282; H01R 24/20; H01R 2201/12

See application file for complete search history.

(56) References Cited

U.S. PATENT DOCUMENTS 6,246,902 B1 * 6/2001 Naylor ................ A61B 5/0428
128/901
6,377,845 B1 4/2002 Kinast
(Continued)

FOREIGN PATENT DOCUMENTS

| EP | 2497418 | 9/2012 |
| WO | 00/65994 | 11/2000 |
| WO | 2017/220328 | 12/2017 |

*Primary Examiner* — Ankit D Tejani
*Assistant Examiner* — Joshua Brendon Solomon

(57) ABSTRACT

The present invention relates to an electrocardiography (ECG) connector comprising two lead wire terminals (40a, 40b), each for connection with a respective signal line of a respective lead wire (204, 205), four measurement terminals (41a, 41b, 42a, 42b), each for connection with a respective measurement line (208a, 208b, 208c, 208d) of a connection cable (208), four resistors (43a, 43b, 44a, 44b), each coupled with their first end to a respective measurement terminal (41a, 41b, 42a, 42b), wherein two resistors (43a, 44a) are coupled with their second end to a first lead wire terminal (40a) and the other two resistors (43b, 44b) are coupled with their second end to the second lead wire terminal (40b), and four voltage clamping elements (45a, 45b, 46a, 46b), each coupled with their first end to a respective measurement terminal (43a, 43b, 44a, 44b) and with their second end to a common coupling point (47).

14 Claims, 5 Drawing Sheets

(51) Int. Cl.
    *A61B 5/282*    (2021.01)
    *H01R 24/20*    (2011.01)

(56)            References Cited

U.S. PATENT DOCUMENTS

| | | | | |
|---|---|---|---|---|
| 2002/0183634 | A1* | 12/2002 | Rantala | A61B 5/0488 |
| | | | | 600/509 |
| 2004/0225210 | A1* | 11/2004 | Brosovich | A61B 5/0428 |
| | | | | 600/372 |
| 2006/0128193 | A1* | 6/2006 | Bradley | H01R 4/5066 |
| | | | | 439/169 |
| 2008/0139953 | A1* | 6/2008 | Baker | A61B 5/04085 |
| | | | | 600/509 |
| 2009/0033333 | A1* | 2/2009 | Gribova | A61B 5/0531 |
| | | | | 324/439 |
| 2011/0313305 | A1* | 12/2011 | Rantala | A61B 5/0428 |
| | | | | 600/509 |
| 2012/0143034 | A1* | 6/2012 | Gaw | A61N 1/048 |
| | | | | 600/393 |
| 2014/0088394 | A1 | 3/2014 | Sunderland | |
| 2017/0251939 | A1* | 9/2017 | Santala | A61B 5/0402 |
| 2017/0281040 | A1* | 10/2017 | McLeod | A61B 5/04286 |
| 2019/0131742 | A1* | 5/2019 | Veenstra | G01R 31/69 |

* cited by examiner

ECG CONNECTOR AND ECG CABLE

CROSS REFERENCE TO RELATED APPLICATIONS

This application claims the benefit of European Patent Application Number 18157601.8 filed Feb. 20, 2018. This application is hereby incorporated by reference herein.

FIELD OF THE INVENTION

The present invention relates to an ECG (electrocardiography) connector and an ECG cable.

BACKGROUND OF THE INVENTION

A typical configuration for a medical-grade ECG measurement system makes use of a measurement unit (e.g. a mobile unit or an ECG monitor), a trunk cable, a trunk unit, a lead set with grabbers or snappers, and ECG electrodes. The electrodes are placed on the body. The lead set connects to the electrodes using snappers or grabbers. Each electrode is connected to the trunk unit via a lead, typically a shielded cable. Inside the grabber or snapper, an inductor is sometimes used to provide enhanced protection and filtering for electrosurgery (ESU) signals. This is important for lead sets used in the operating theatre. Inside the trunk, safety resistors are often placed to protect the measurement unit against high voltages that can occur during defibrillation treatments. Additional safety elements such as sidactors are used inside the measurement unit to limit the maximum voltage on the input of the ECG measurement unit.

Currently, dedicated Operating Room (OR) and Intensive Care Unit (ICU) ECG lead sets (which are the standard leads sets used outside the OR) are available and in use. If a patient is moved to surgery (where an electrosurgery (ESU) knife may be used) the ICU lead set is disconnected and an OR lead set is applied to the patient. Besides the inconvenience, this lead set replacement can take several minutes and imposes a safety risk because during lead set replacement the patients' electrocardiogram cannot be monitored. The reason for a dedicated OR lead set is that the OR lead set provides extra filtering to attenuate the ESU knife signal towards the monitor, implemented by a higher resistor value and inductor in all ECG leads. With this high-impedance (resistor+inductor)-network in each lead it is not possible to measure respiration via ECG electrodes because the respiration modulation signal is strongly attenuated across the lead set impedance while also the respiration signal is hampered by high noise levels. During surgery this is not an issue as respiration is monitored in different ways, but before and after surgery this respiration signal must also be measured and thus the standard lead set must be used, which does not have the ESU filter inside.

The trunk cable has a large trunk box at the end where the lead set is connected. The size of the trunk box is for a large part dominated by the physical size of the protection resistors. The protection resistors are specified to support a specific energy and voltage that can occur from defibrillation pulses applied to the patient. The resistor values are low enough to support respiration measurements via ECG electrodes, limiting the maximum value of the resistors and therefore leading to physically large resistor sizes due to the higher energy rating needed for lower resistor values to absorb more energy during a defibrillation shock. The trunk cable is used in combination with the OR and ICU lead sets and provides sufficient protection for defibrillation pulses but not for ESU knifes. The trunk cable has relatively low-Ohmic protection resistors inside the trunk box (e.g. typical value 1 k$\Omega$ or 3.3 k$\Omega$, one per ECG lead).

As already mentioned above there are ECG special lead sets which are only used in the OR. These provide protection against the ESU knife. However, with these lead sets it is not possible to measure respiration via the ECG electrodes. During surgery, respiration is monitored in different manners, but before and after a surgery there is a need to change the lead set as respiration can then be monitored via the ECG measurement system. Hence, there is a need for a solution that avoids the need to change the lead set.

SUMMARY OF THE INVENTION

It is an object of the present invention to provide an ECG connector and an ECG cable, which avoid the need to change the lead set before and after surgery to enable respiration measurement.

In a first aspect of the present invention an ECG connector is presented comprising:

two lead wire terminals, each for connection with a respective signal line of a respective lead wire, four measurement terminals, each for connection with a respective measurement line of a connection cable, four resistors, each coupled with their first end to a respective measurement terminal, wherein two resistors are coupled with their second end to a first lead wire terminal and the other two resistors are coupled with their second end to the second lead wire terminal, and four voltage clamping elements, each coupled with their first end to a respective measurement terminal and with their second end to a common coupling point.

In a further aspect of the present invention an ECG cable is presented comprising:

an ECG connector as disclosed herein, two lead wires connected with the two lead wire terminals of the ECG connector, and two ECG electrode connectors, each for connection with a respective ECG electrode.

Preferred embodiments of the invention are defined in the dependent claims. It shall be understood that the claimed ECG cable has similar and/or identical preferred embodiments as the claimed ECG connector, in particular as defined in the dependent claims and as disclosed herein.

The present invention is based on the idea to provide a universal ECG connector and ECG cable (representing a new lead set), which provide safety levels for use with ESU knifes while also supporting respiration measurement via the ECG electrodes. A key benefit is that the universal ECG connector and ECG cable avoid the need to change the lead set before and after surgery, thereby saving time. Moreover, the proposed ECG connector and ECG cable achieve a substantial reduction of the physical size of the conventional trunk box (which is replaced by the proposed ECG connector), enabled by the reduced physical size of the resistors inside the ECG connector. For a higher resistor value a lower energy rating is needed.

The ECG connector incorporates the safety network comprising resistors and voltage clamping elements (preferably sidactors; alternatively neons or trigards), and optionally inductors. The proposed ECG connector and ECG cable can be used with existing measurement units (e.g. ECG monitors or mobile unit) provided that these support 4-wire respiration measurement topologies.

In an embodiment the ECG connector further comprises a shield terminal for connection with a shield of the connection cable, wherein the shield terminal is connected with the common coupling point. The shield provides for a reduction of the sensitivity to interference.

In another embodiment the ECG connector further comprises two inductors, each coupled between a respective lead wire terminal and the respective second ends of two respective resistors. This inductors provide enhanced protection and filtering for ESU signals.

In another embodiment one or more of the resistors comprises two or more resistor elements coupled in series. For instance, multiple lower-value resistor elements can be used in series to allow for an attractive low-cost connector design. The resistor elements can then also be reduced in size compared to a single resistor.

The resistors may each have a resistance of at least 2 k$\Omega$, in particular in the range of 2 k$\Omega$ to 50 k$\Omega$ or in the range of 5 k$\Omega$ to 20 k$\Omega$, e.g. 10 k$\Omega$, By using a 4-wire respiration measurement topology the protection resistance in the lead sets can be increased from 1 k$\Omega$ (e.g. the typical value used in lead sets that support respiration measurement) to a higher value, e.g. 10 k$\Omega$ (e.g., the typical value currently used in the dedicated OR lead sets that are ESU safe), while supporting respiration measurement. A 10 k$\Omega$ protection resistor dissipates substantially less energy compared to the 1 k$\Omega$ resistor for a given resistor voltage. Therefore, protection resistors of substantially smaller physical size can be used, which brings as an additional benefit that the size of the lead set trunk box is strongly reduced (even with the needed increase of resistors amounts).

The ECG connector may be configured as trunk connector for connection between a connection cable for connection to a measurement unit, in particular an ECG monitor, and ECG lead wires for connection with ECG electrodes.

The ECG connector may further comprise one or more additional lead wire terminals, and, per additional lead wire terminal, at least one additional measurement terminals, one additional resistor, and one additional voltage clamping element. In this way even more ECG electrodes can be coupled to the ECG connector to provide e.g. a 5 (or 6) lead ECG or a 12 lead ECG.

In another embodiment the ECG connector may further comprise two, three, four or six additional lead wire terminals, and, per set of two additional lead wire terminals, four additional measurement terminals, four additional resistors, and four additional voltage clamping elements. This provides that some more or all ECG electrodes may be able to support respiration measurement and can be used universally.

The proposed ECG cable comprises an ECG connector as described herein, two or more lead wires connected with the two or more lead wire terminals of the ECG connector, and two or more ECG electrode connectors, each for connection with a respective ECG electrode. The ECG electrode connector may be configured as snappers or grabbers, which are both commonly used as ECG electrode connectors. They are electrically equivalent, and the choice between grabber or snapper depends on the preference of the user. Herein, reference is generally made to ECG electrode connector, and all technical details apply to all embodiments, including snappers, grabbers or clamping means, if not specified otherwise. They generally comprise a connection arrangement for mechanically connecting the ECG electrode connector with an ECG electrode.

The proposed ECG cable may comprise two or more ECG connectors, wherein at least one ECG connector is an ECG connector as disclosed herein. This enables multiple different uses of the ECG cable.

Further, in one embodiment the ECG cable may further comprise a cable and a connector for connecting the ECG connector with an ECG measurement module.

Still further, in an embodiment the ECG cable may further comprise an extender coupled between the connector and the ECG measurement module, an extender cable connected to the extender, an extender ECG connector connected to the extender cable, one or more lead wires connected with one or more lead wire terminals of the ECG connector, and one or more ECG electrode connectors, each for connection with a respective ECG electrode. The extender enables extension of the number of electrodes without the need to disconnect the already placed electrodes connected to the (first) ECG connector. The number of electrodes added by the extender is at least one. The extender acts as a feed-through for the measurement signals provided to the terminals of the first ECG connector.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
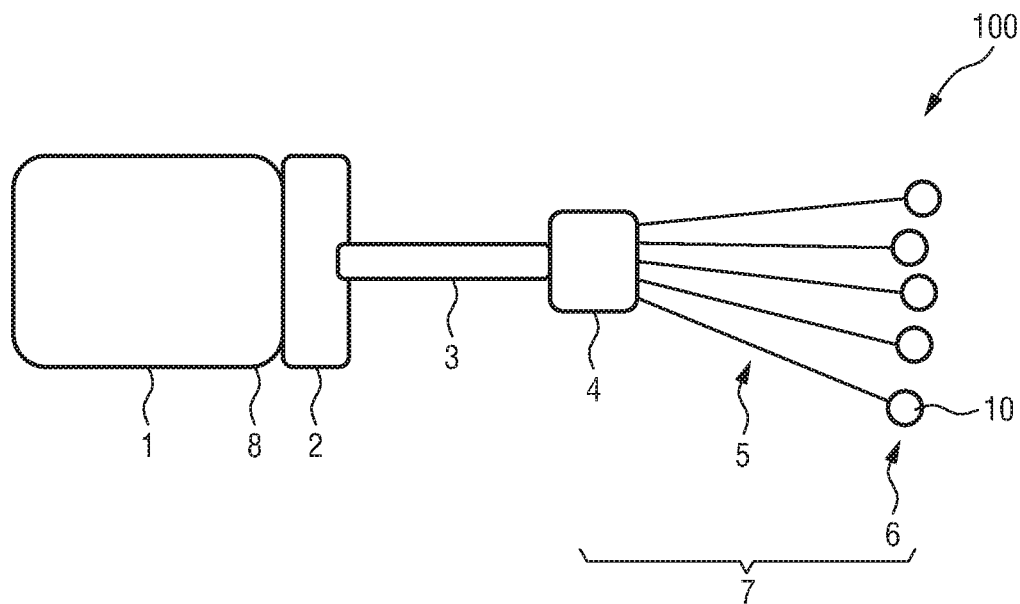
FIG. 1 shows a schematic diagram of an embodiment of a measurement system according to the present invention.

FIG. 1 shows a schematic diagram of an embodiment of an ECG measurement system 100 according to the present invention, in this example using a 5-lead ECG configuration. The ECG measurement system 100 comprises the ECG measurement module 1, which is connected to the (in this example five) ECG electrodes 10 via a connector 2, cable 3, ECG connector 4 (trunk box) of the present invention, (five) ECG leads 5 and (five) ECG electrode connectors 6 (e.g. grabbers or snappers). The ECG connector 4, the ECG leads 5 and the ECG electrode connectors 6 together represent an ECG cable 7 according to the present invention.

One element of the present invention is the replacement of the typically used 2-wire respiration detection system by a 4-wire respiration detection system and interface. The new ECG cable provides dual connections and protection elements for each electrode that potentially is used for respiration measurement (e.g. typically the connections to electrodes RA, LA and LL). The number of electrodes does not need to be increased.

A second element of the present invention is the replacement of the protection resistors in the trunk box. The standard trunk box uses protection resistors of typically 1 kΩ. In the proposed implementation the resistors are increased, in an exemplary embodiment to about 10 kΩ, thereby reducing the energy dissipated in the resistors during defibrillation and ESU events, thus enabling the use of resistors of reduced physical size without loss of safety.

The proposed ECG connector realizes a universal lead set that provides protection against defibrillation pulses and ESU knifes when used in combination with the inductors implemented in the OR ECG (of 6.8 mH typical value), while enabling respiration measurement via the ECG electrodes.

Protection resistors of e.g. 10 kΩ are assumed to be inside the ECG connector 4. In an exemplary embodiment eight resistors are provided in the ECG connector 4: two for each lead 5 that can be used for respiration measurement (RA, LA, LL); one for each lead not used for respiration (RL, V1). Inductors of e.g. typically 6.8 mH are optionally present either in the ECG connector or in the ECG electrode connectors 6 as part of the ESU filter.

Movement from the chest due to a person's respiration varies the electrical impedance of the body evaluated between two points. The variation is largest close to the lungs, where the expansion of the body is largest. This is also near the position where usually one or more ECG electrodes are placed. Respiration can thus be measured via the ECG electrodes, by evaluating the electrical impedance between two electrodes. Typically, two electrodes out of the three electrodes (RA, LA and LL) are used, in combinations that are patient-dependent.

Figure 2:
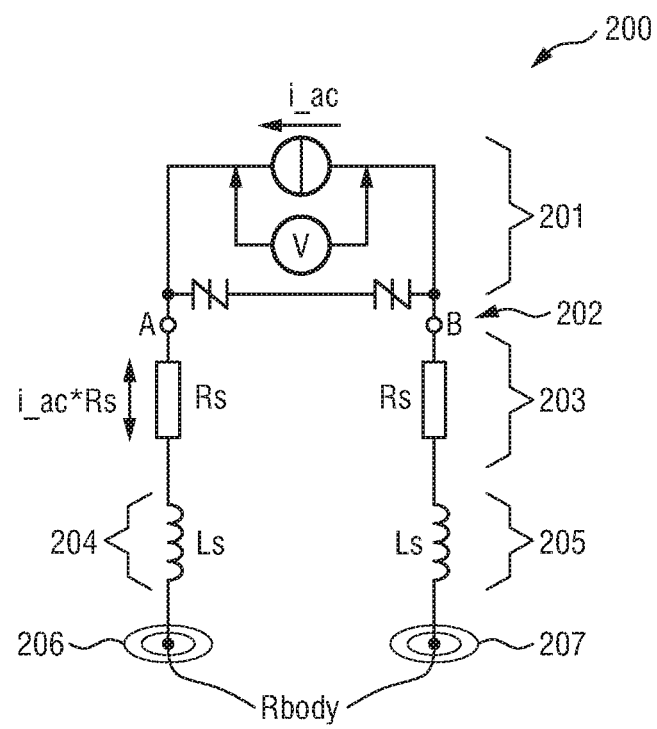
FIG. 2 shows a circuit diagram of an embodiment of a known respiration measurement system.

To evaluate the impedance between two electrodes, a 2-wire or a 4-wire measurement system can be used. FIG. 2 shows a circuit diagram of an embodiment of a known 2-wire respiration measurement system 200. It comprises an impedance measurement unit 201, a connector 202, a trunk box 203 (including protection resistors Rs), ECG electrode connectors 204, 205 (including ESU filtering inductors Ls) and ECG electrodes 206, 207. The respiration impedance measurement system (inside the impedance measurement unit) drives an AC-current i_ac to the patient's body and measures the resulting voltage V across nodes A, B. The actual measured impedance is the series impedance of Rbody+2·Z_electrode+2·Z_Ls+2 Rs. The voltage clamping elements are conventionally placed inside the impedance measurement unit 01. The ESU protection inductors Ls may be embedded in the trunk box 203 or in the ECG electrode connectors 204, 205. The trunk box 203 includes the safety series resistors Rs.

In a 2-wire respiration measurement system, the resistors Rs have a typical value of at least Rs=1 kΩ. For a higher number of leads, Rs=1 kΩ may be used for leads that shall be used for respiration measurements and Rs=3 kΩ may be used for leads that shall not be used for respiration measurements. A larger protection resistor results in less accurate measurements because the maximum current to the patient is limited by the total series resistance, and because the relative variation of the body impedance from respiration compared to the total measured impedance is small. Lower-Ohmic resistors Rs are preferred for accurate Rbody measurement, but dissipate more energy when a patient is undergoing defibrillation treatments and thus need to be large in physical size.

Figure 3:
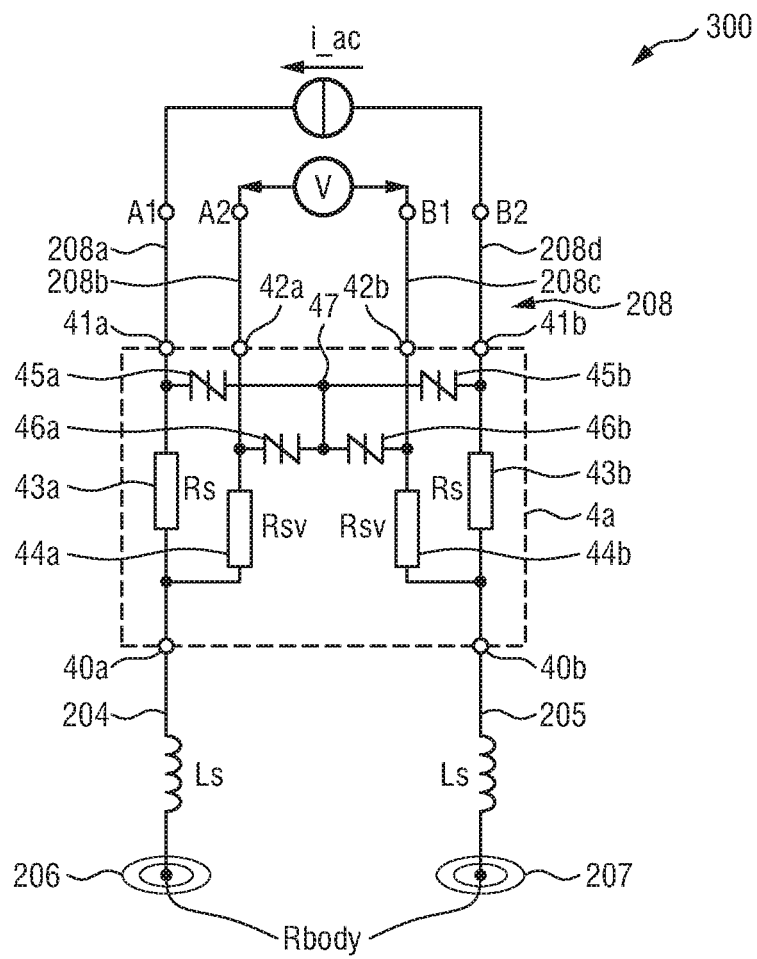
FIG. 3 shows a circuit diagram of a first embodiment of a respiration measurement system including a first embodiment of an ECG connector according to the present invention.

FIG. 3 shows a circuit diagram of a first embodiment of a respiration measurement system 300 in a 4-wire measurement configuration including a first embodiment of an ECG connector 4a according to the present invention. The ECG connector 4a comprises two lead wire terminals 40a, 40b, each for connection with a respective signal line of a respective lead wire 204, 205. Four measurement terminals 41a, 41b, 42a, 42b are provided, each for connection with a respective measurement line 208a, 208b, 208c, 208d of a connection cable 208. Four resistors 43a, 43b (Rs) and 44a, 44b (Rsv) are provided, wherein each of them is coupled with their first end to a respective measurement terminal 41a, 41b, 42a, 42b. Further, two resistors 43a, 44a are coupled with their second end to a first lead wire terminal 40a and the other two resistors 43b, 44b are coupled with their second end to the second lead wire terminal 40b. Four voltage clamping elements 45a, 45b, 46a, 46b (e.g. sidactors) are provided, each coupled with their first end to a respective measurement terminal 41a, 41b, 42a, 42b and with their second end to a common coupling point 47. The sidactors are shown as located in the ECG connector 4a, but may alternatively be located in the measurement unit (monitor).

The voltage drop across resistors 43a, 43b (Rs) is not part of the measured impedance. This is because an extra set of wires is used to probe the voltage at the ECG electrodes 206, 207, at the other end of the protection network that may exist in the modulation path. The measured impedance equals the body impedance Rbody plus the series impedance of the two ECG electrodes 206, 207 and the series impedance of the two (optional) inductors Ls. The resistors 44a, 44b (Rsv) are installed to provide protection, but these do not add to the measured impedance because there is no (modulation) current in these resistors. This makes the 4-wire measurement system a lot more accurate compared to the 2-wire measurement system, and it is therefore of interest to design an ECG cable that supports 4-wire impedance measurements. As seen in FIG. 3, the 4-wire configuration does not require extra electrodes but makes use of dual wires and protection elements for each ECG electrode that (potentially) is used for the impedance measurement.

Since the 4-wire configuration is not hampered by losses in Rs or Rsv, the value of Rs and Rsv can be increased (for example, from typically 1 kΩ to typically 10 kΩ) with minimal loss of accuracy in the impedance measurement. The value of the resistor Rs can be increased up to a value where the resistor Rs starts to limit the modulation current to the patient. The value of the resistor Rsv can be increased even further provided that its noise contribution (to a measured respiration signal) remains acceptable. Rs=Rsv=10 kΩ has been found to provide satisfactory performance in a practical system.

When the patient is undergoing a defibrillation treatment, part of the energy will be dissipated in the resistors Rs and Rsv via the resistor-sidactor network. The energy dissipated in the resistors reduces for increased resistors, and thus it becomes possible to use resistors with reduced energy rating when the resistor value is increased, which are usually smaller in size. A smaller resistor enables a smaller ECG connector, which is an important advantage for patient comfort. Moreover, the new implementation can also include the voltage clamping elements 45a, 45b, 46a, 46b (e.g. sidactors; alternatively neons or trigards) which form part of the protection network but are usually placed inside the monitor. In summary, the ECG connector can thus be substantially reduced in size compared to known ECG connectors or trunk boxes.

Figure 4:
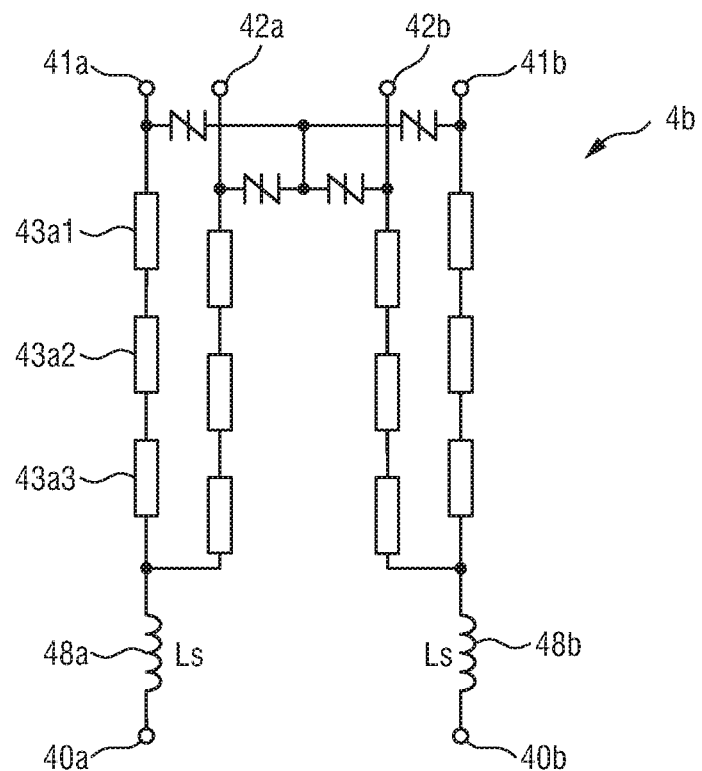
FIG. 4 shows a circuit diagram of a second embodiment of an ECG connector according to the present invention.

FIG. 4 shows a circuit diagram of a second embodiment of an ECG connector 4b according to the present invention. Compared to the first embodiment of the ECG connector 4a shown in FIG. 3, the ECG connector 4b comprises, per ECG electrode, an inductor 48a, 48b, each of which being connected between the respective lead wire terminal 40*a*, 40*b* and the respective resistors Rs, Rsv. The inductors 48*a*, 48*b* provide protection and filtering for ESU signals.

Further, each of the resistors Rs, Rsv is split up into several resistor elements. For instance, the resistor 43*a* is split up into three resistor elements 43*a*1, 43*a*2, 43*a*3 connected in series. The other resistors 44*a*, 43*b*, 44*b* are realized by series coupling of resistor elements as well. The number of resistor elements per resistor may be different from three. Generally, n resistor elements (n=3 in the exemplary embodiment shown in FIG. 4) are used in series, each of value Rs/n and Rsv/n. The energy dissipation per resistor element and voltage across each resistor reduces proportionally with n, and therefore each resistor element can be much smaller and cheaper, leading to a more compact and cheaper overall solution for the ECG connector. Moreover, the series connection can be constructed in an arbitrary physical configuration (e.g. straight, circular, etc.) which allows for a more attractive design of the ECG connector.

Figure 5:
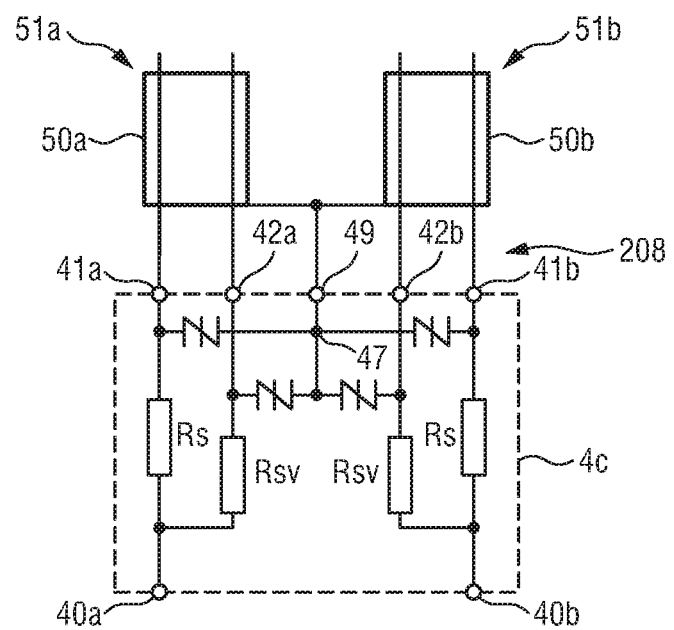
FIG. 5 shows a circuit diagram of a third embodiment of an ECG connector according to the present invention.

FIG. 5 shows a circuit diagram of a third embodiment of an ECG connector 4*c* according to the present invention. Compared to the first embodiment of the ECG connector 4*a* shown in FIG. 3, the ECG connector 4*c* comprises a shield terminal 49 for connection with a shield 50*a*, 50*b* of the connection cable 51*a*, 51*b*. The shield terminal 49 is connected with the common coupling point 47 of the ECG connector 4*c*. Shielding against interferences is thus provided.

Figure 6:
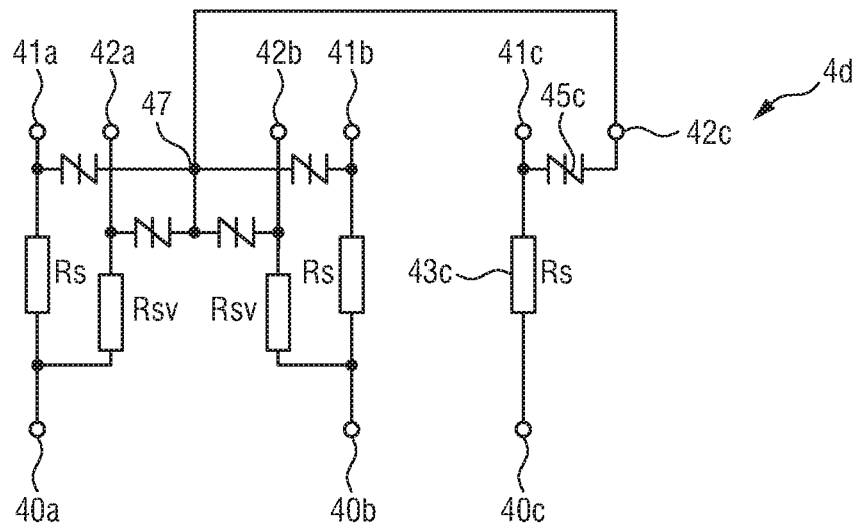
FIG. 6 shows a circuit diagram of a fourth embodiment of an ECG connector according to the present invention.

FIG. 6 shows a circuit diagram of a fourth embodiment of an ECG connector 4*d* according to the present invention. Compared to the first embodiment of the ECG connector 4*a* shown in FIG. 3, the ECG connector 4*d* comprises one (or more) additional lead wire terminal 40*c* and, per additional lead wire terminal, one or two additional measurement terminals 41*c*, 42*c* (wherein the terminal 42*c* may preferably be coupled to the common coupling point 47, which is coupled to a shield of a connection cable; i.e., the terminal 42*c* may not be regarded as a measurement terminal), one additional resistor 43*c* and one additional voltage clamping element 45*c*. In this way one (or more) ECG electrode(s) can be coupled to the ECG connector 4*d*.

Figure 7:
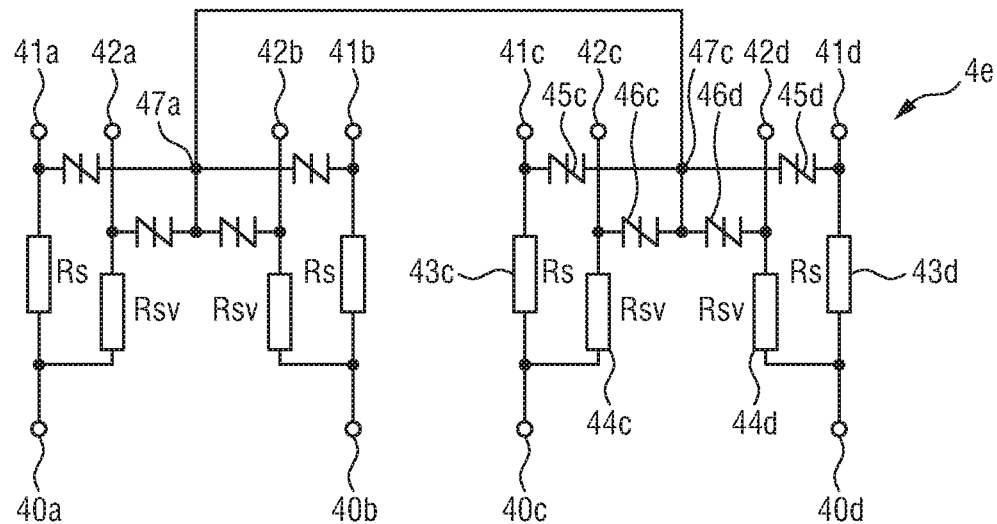
FIG. 7 shows a circuit diagram of a fifth embodiment of an ECG connector according to the present invention.

FIG. 7 shows a circuit diagram of a fifth embodiment of an ECG connector 4*e* according to the present invention. Compared to the first embodiment of the ECG connector 4*a* shown in FIG. 3, the ECG connector 4*e* comprises two (or four or six or even more) additional lead wire terminals 40*c*, 40*d*. Further, per set of two additional lead wire terminals, four additional measurement terminals 41*c*, 42*c*, 41*d*, 42*d*, four additional resistors 43*c*, 44*c*, 43*d*, 44*d*, and four additional voltage clamping elements 45*c*, 46*c*, 45*d*, 46*d* are provided, i.e. the ECG connector 4*a* is doubled (or tripled or multiplied by another integer). The common coupling points 47*a* and 47*c* are preferably connected (and coupled to a shield of a connection cable). All ECG electrodes can thus support respiration measurement and can be used universally.

Figure 8:
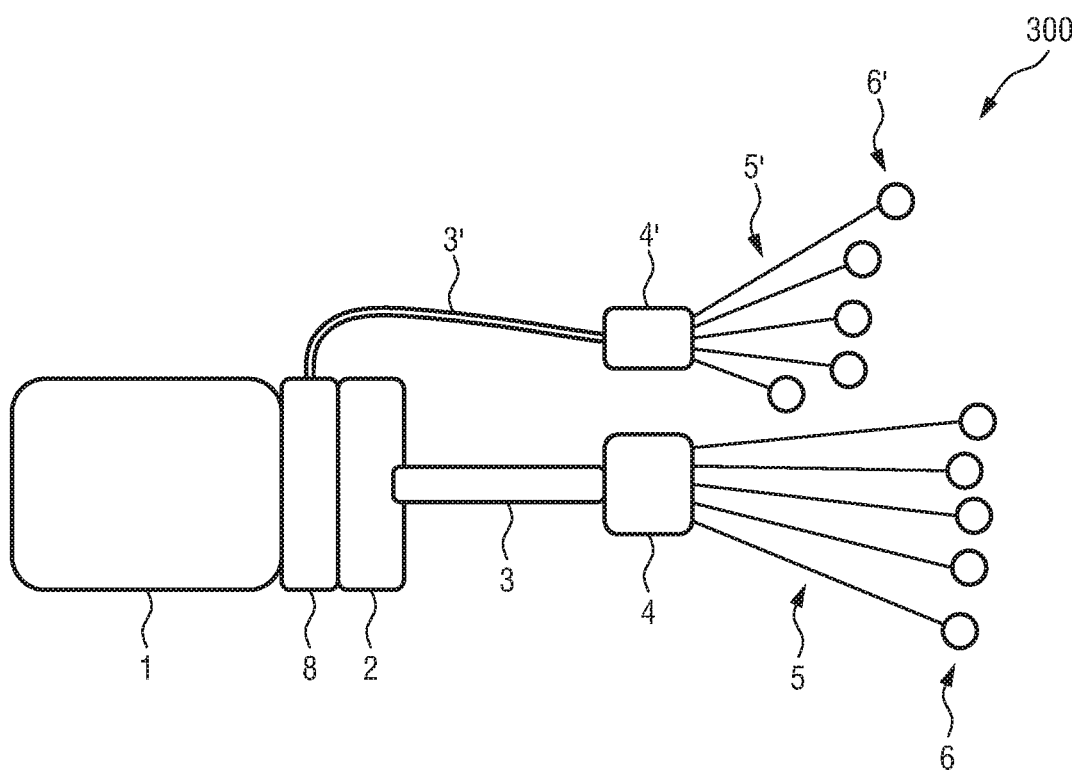
FIG. 8 shows a schematic diagram of another embodiment of a respiration measurement system according to the present invention.

FIG. 8 shows a schematic diagram of another embodiment of a respiration measurement system 300 according to the present invention, which provides a flexible extension of the measurement. Compared to the system 100 shown in FIG. 1, the system 300 further comprises an optional adapter 8 to extend the number of ECG leads. For example, a 5 (or 6) lead ECG lead set 5 can be extended to 12 lead ECG lead set by using the adapter (also called extender), which is able to connect another (extender) lead ECG lead set 5' with (extender) ECG electrode connectors 6' via another cable 3' and (extender) ECG connector 4', which may be an ECG connector as disclosed herein or a conventional trunk box. The extender lead set 5' extends the total number of ECG electrodes by at least one. The adapter 8 implements a feed-through for the measurement connections of the main ECG measurements provided via the ECG connector and the cable 3 to the connector 2. The ECG connector 4' preferably has protection elements inside for protecting the electrodes 6'.

Further variations of the system are possible. For instance, an embodiment of the ECG connector may support 4-wire respiration measurements and 5-lead ECG measurements. The 5-lead ECG connector 4 supporting 4-wire respiration is small in size. It has 8 resistors and sidactors. The extender ECG connector 4' may have 5 resistors and sidactors and may be even smaller. The overall solution may thus be implemented with attractive small and light-weight trunk boxes (ECG connectors). Such trunk boxes are well suited in mobile ECG measurement applications, where the patient has to carry the trunk boxes.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An electrocardiography (ECG) connector, comprising:
   two lead wire terminals, each for connection with a respective signal line of a respective lead wire;
   four measurement terminals each adapted for measuring respiration, wherein each of the four measurement terminals is connected with a respective measurement line of a connection cable;
   four resistors, each having a resistance that does not limit a modulation current from a patient, and each being coupled with its first end to a respective measurement terminal, wherein two resistors are coupled with their second end to a first lead wire terminal and the other two resistors are coupled with their second end to a second lead wire terminal; and
   four voltage clamping elements, each coupled with their first end to a respective measurement terminal and with their second end to a common coupling point.

2. The ECG connector as claimed in claim 1, further comprising a shield terminal for connection with a shield of the connection cable, wherein the shield terminal is connected with the common coupling point.

3. The ECG connector as claimed in claim 1, further comprising two inductors, each coupled between a respective lead wire terminal of the two lead wire terminals and the respective second ends of two respective resistors of the four resistors.

4. The ECG connector as claimed in claim 1, wherein one or more of the four resistors includes two or more resistor elements coupled in series.

5. The ECG connector as claimed in claim 1, wherein the resistors each have a resistance of at least 2 kΩ.

6. The ECG connector as claimed in claim 1, wherein the ECG connector is configured as trunk connector for connection between a connection cable for connection to a measurement unit, and ECG lead wires for connection with ECG electrodes.

7. An electrocardiography (ECG) cable, comprising:
an ECG connector as claimed in claim 1;
two lead wires connected with the two lead wire terminals of the ECG connector; and
two ECG electrode connectors, each for connection with the ECG connector and a respective ECG electrode.

8. The ECG cable as claimed in claim 7, further comprising at least one additional ECG connector coupled to the common coupling point.

9. The ECG cable as claimed in claim 7, further comprising a cable and a connector for connecting the ECG connector with an ECG measurement module.

10. The ECG cable as claimed in claim 9, further comprising:
an extender coupled between the ECG connector and the ECG measurement module;
an extender cable connected to the extender;
an extender ECG connector connected to the extender cable;
one or more lead wires connected with one or more lead wire terminals of the extender ECG connector; and
one or more ECG electrode connectors, each for connection with the extender ECG connector and a respective ECG electrode.

11. The ECG connector as claimed in claim 1, further comprising:
one or more additional lead wire terminals, and
per additional lead wire terminal, at least one additional measurement terminal, one additional resistor, and one additional voltage clamping element.

12. The ECG connector as claimed in claim 1, further comprising:
two, three, four or six additional lead wire terminals, and
per set of two additional lead wire terminals, four additional measurement terminals, four additional resistors, and four additional voltage clamping elements.

13. The ECG connector as claimed in claim 1, wherein the resistors each have a resistance that is greater than 1 kΩ.

14. The ECG connector as claimed in claim 1, wherein the resistors each have a resistance in a range of 2 kΩ to 10 kΩ.

* * * * *